United States Patent [19]

Blais et al.

[11] Patent Number: 4,462,410
[45] Date of Patent: Jul. 31, 1984

[54] SPIROMETER

[75] Inventors: Maurice R. Blais, Andover; Craig N. Hess, Chestnuthill, both of Mass.

[73] Assignee: LSE Corp., Woburn, Mass.

[21] Appl. No.: 277,998

[22] Filed: Jun. 26, 1981

[51] Int. Cl.³ .............................................. A61B 5/08
[52] U.S. Cl. .................................... 128/727; 272/99
[58] Field of Search .............................. 128/725–727, 128/730; 272/99; 73/239, 262; 346/33 ME, 46

[56] References Cited

U.S. PATENT DOCUMENTS

| | | | |
|---|---|---|---|
| 2,999,495 | 9/1961 | Shipley | 346/33 ME X |
| 3,081,766 | 3/1963 | Dubsky et al. | 128/725 |
| 3,385,295 | 5/1968 | Beasley | 128/145.8 |
| 3,395,699 | 8/1968 | Beasley | 128/2.08 |
| 3,555,555 | 1/1971 | Lambert | 346/30 |
| 3,559,639 | 2/1971 | Nagus et al. | 128/2.08 |
| 3,589,190 | 6/1971 | Jones | 73/262 X |
| 3,653,374 | 4/1972 | Talonn et al. | 346/33 ME X |
| 3,659,590 | 5/1972 | Jones et al. | 128/2.08 |
| 3,680,378 | 8/1972 | Aurillo et al. | 73/231 R |
| 3,693,180 | 9/1972 | Hasebe et al. | 346/46 X |
| 3,703,893 | 11/1972 | Hardway, Jr. | 128/2.08 |
| 3,713,436 | 1/1973 | Hardway, Jr. | 128/2.08 |
| 3,718,136 | 2/1973 | Blum | 128/725 X |
| 3,722,506 | 3/1973 | McMillan, Jr. | 128/727 |
| 3,726,271 | 4/1973 | Mondshine et al. | 128/2.08 |
| 3,946,726 | 3/1976 | Pikul | 128/2.08 |
| 3,985,124 | 10/1976 | Coleman | 128/2.08 |
| 4,010,761 | 3/1977 | Tipple | 128/145.6 |
| 4,041,935 | 8/1977 | Garbe | 128/2.08 |
| 4,112,931 | 9/1978 | Burns | 128/2.08 |
| 4,172,258 | 10/1979 | Lane | 346/46 |
| 4,307,729 | 12/1981 | Hart et al. | 128/727 |

Primary Examiner—Lee S. Cohen
Assistant Examiner—Angela D. Sykes
Attorney, Agent, or Firm—Kenway & Jenney

[57] ABSTRACT

A recording spirometer for performing both a single breath test and a maximum voluntary ventilation test. The spirometer includes a housing in which is disposed a pusher plate. This pusher plate is supported by a member constrained by rotary bearings to move in substantially a straight line. An elastomeric seal creates an airtight chamber beneath the pusher plate. The supporting member also carries a recording medium support so that a permanent record may be made of the volume of exhaled air as a function of time. For performing the maximum voluntary ventilation test, the apparatus includes a mechanism for supporting the pusher plate at an intermediate position so that both inhalation and exhalation segments may be measured and recorded. A rotatable turret is provided for carrying a plurality of pens for marking the recording medium so that different colors may be used for different tests. The rotatable turret is carried on a marking assembly which is driven across the recording medium at a constant rate of speed so that volumetric flow as a function of time may be recorded.

14 Claims, 5 Drawing Figures

U.S. Patent  Jul. 31, 1984  Sheet 2 of 2  4,462,410
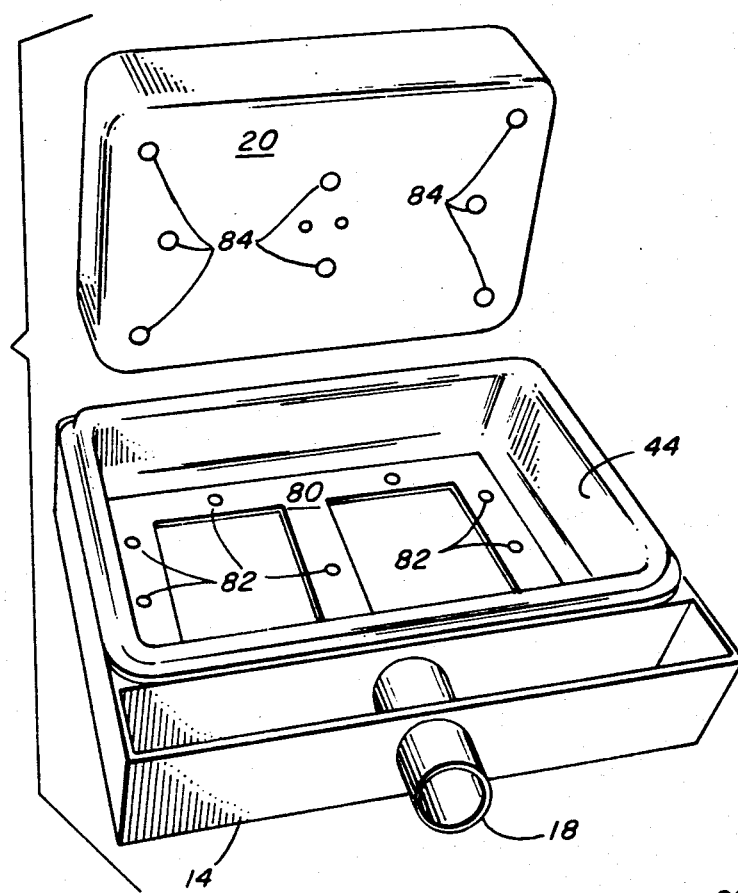
FIG. 4
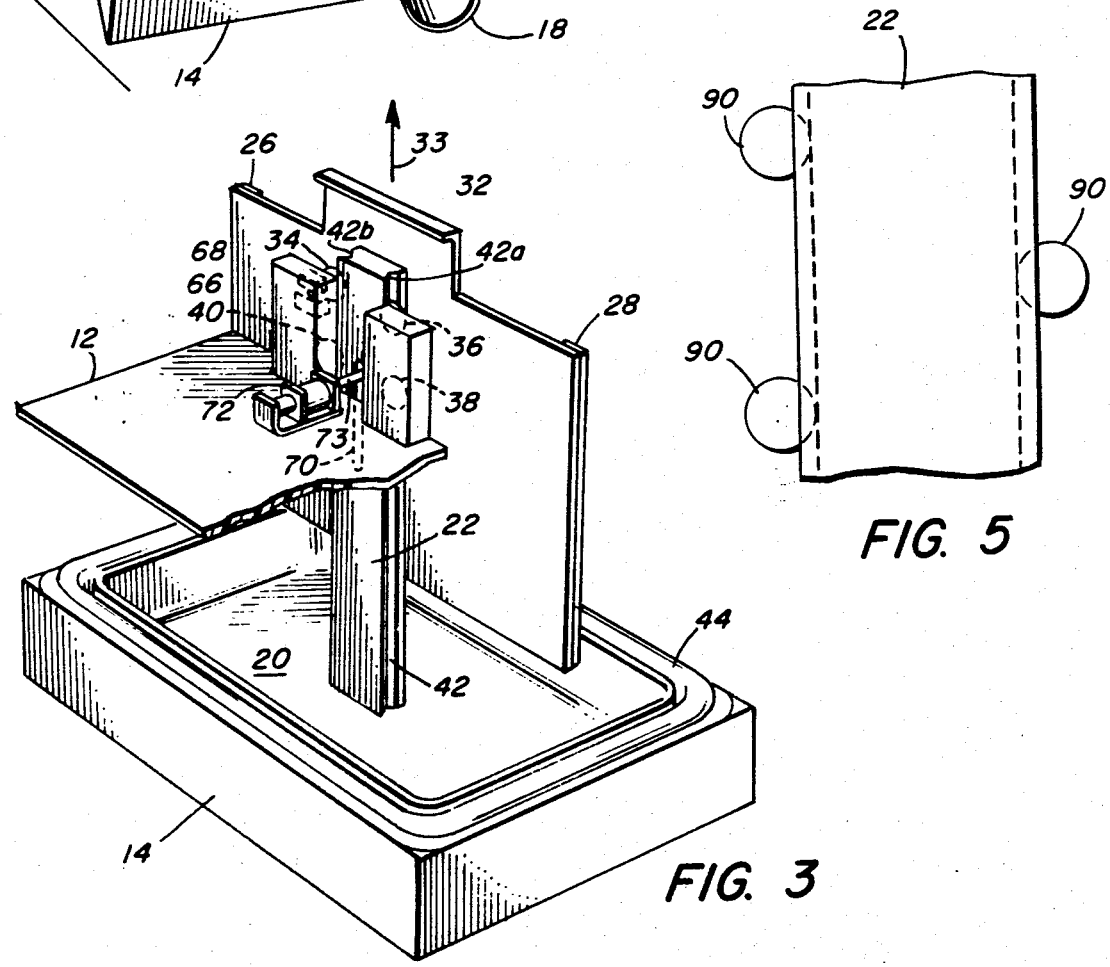
FIG. 5
FIG. 3

SPIROMETER

BACKGROUND OF THE INVENTION

The present invention relates to spirometers and more particularly to a recording spirometer capable of performing a single expiratory breath test and multiple breath expiratory and inspiratory tests such as a measurement of maximum voluntary ventilation or of tidal volume.

In general, spirometers measure physiological parameters associated with breathing. These parameters include lung volumes and the rates at which air is inhaled and exhaled. Among the tests which spirometers typically perform are the forced vital capacity test, slow vital capacity test, the measurement of the subdivisions of lung volume such as tidal volume and expiratory reserve volume and the measurement of maximum voluntary ventilation. In the forced vital capacity test, the subject takes a deep breath and then exhales as rapidly as possible into the spirometer so that the volume of exhaled air as a function of time is measured. In some cases, this exhalation is followed by a maximum inhalation. In the maximum voluntary ventilation test the subject continuously exhales and inhales at a maximum rate for a specified period of time, the spirometer recording the rates of outflow and inflow as a function of time.

Spirometers are known in which a piston moves within an expansible chamber as exhaled air flows into the apparatus. The piston may carry a card or other recording medium which is marked by a pen travelling at a uniform rate across the card so that the combination of motion of the piston and the pen creates a graph of expiratory flow as a function of time. With these devices, however, the measurement of inspiratory as well as expiratory volumes cannot be performed since such a measurement requires bidirectional motion of the piston so as to accommodate a subject who inhales a larger volume of air than he originally exhaled into the spirometer. Spirometers are also subject to inaccuracies, oftentimes due to the manner of supporting the piston for motion within the spirometer housing. Furthermore, it is often desired to perform two or more different tests and to record the results on the same card using pens of different colors. In the known recording spirometers it has been necessary to remove one pen and insert a pen of a different color before performing a later test. This change of pen required recalibrating the position of the newly inserted pen with respect to the recording medium before the beginning of the next test.

It is therefore an object of the present invention to provide a spirometer which is highly accurate and reliable and yet of simple and inexpensive construction.

It is a further object of this invention to provide a spirometer which is capable of performing not only a single breath expiratory test but also the measurement of both expiratory and inspiratory volumes.

A still further object of this invention is a recording spirometer which permits the use of different colored marking instruments without necessitating recalibration as colors are changed.

It is yet another object of this invention to provide a spirometer in which the components exposed to a subject's exhaled air may be easily removed for cleaning and sterilization.

Other objects, features and advantages of this invention will be pointed out in what follows.

SUMMARY OF THE INVENTION

The foregoing objects, according to this invention, are achieved by a recording spirometer including a housing having an upper portion and a lower portion. A pusher plate, having a top side and a bottom side is disposed within the housing, and sealing apparatus is provided for creating an airtight seal between the pusher plate and the housing. The pusher plate is supported by an elongate supporting member affixed to the top side of the pusher plate. Bearings supported by the housing engage the supporting member so as to constrain it and the attached pusher plate to substantially linear motion along a reference axis to create beneath the bottom side of the pusher plate an airtight chamber whose volume varies with the position of the pusher plate within the housing. The lower portion of the housing includes an opening adapted for the introduction of exhaled air into the airtight chamber. A recording medium support element is mounted on the supporting member so as to move linearly with the pusher plate. Marking apparatus is mounted to move at a constant rate along an axis perpendicular to the reference axis. In this way, the concurrent motion of the pusher plate and the marking apparatus creates a graph of the volume of expired air as a function of time.

In a preferred embodiment the marking apparatus includes a rotatable turret particularly adapted for holding a plurality of marking instruments. The marking apparatus in this embodiment is slidingly supported on a shaft affixed to the housing and is moved across the recording medium by a motor driven flexible belt. The preferred seal is a molded elastomeric rolling seal disposed adjacent to the bottom side of the pusher plate. The edges of this seal are clamped between the upper and lower housing portions.

The elongate supporting member is restrained by guides including a first pair of spaced apart roller bearings disposed on one side of the elongate supporting member and a second pair of spaced apart rollers disposed on the opposite side of the supporting member. These rollers are adapted to fit into grooves in the sides of the elongate supporting member. Alternatively, the supporting member may be constrained by means of a pair of spaced apart rollers disposed on one side of the member, and a single roller disposed on the opposite side of the supporting member approximately half way between the pair of spaced apart rollers. As before, these rollers are adapted to fit into grooves in the sides of the elongate supporting member. A switch mounted for activation upon movement of the pusher plate is included to initiate the motor driven belt.

In another embodiment particularly adapted for performing tests requiring both expiratory and inspiratory maneuvers such as the maximum voluntary ventilation test, the spirometer further includes apparatus adapted to support the pusher plate at an intermediate position above its lowest resting position at the beginning of the test. This embodiment also includes equipment for maintaining the seal in intimate contact with the pusher plate throughout the measurement. The pusher plate is maintained at the intermediate position by means of a solenoid mounted so as to engage in its extended state a slot in the rear side of the elongate supporting member. The seal, preferably a molded elastomeric rolling seal, has a ferromagnetic plate member secured to its inner surface. This plate is attracted to a plurality of spaced apart permanent magnets secured to the bottom of the pusher plate so that the seal and pusher plate remain together throughout the measurement of maximum voluntary ventilation.

BRIEF DESCRIPTION OF THE DRAWING

The recording spirometer disclosed herein will be better understood with reference to the following drawing of which:

FIG. 3 is a perspective view, partially cut away, of the spirometer;

FIG. 4 is an exploded view of the pusher plate and rolling seal of the spirometer; and FIG. 5 is an elevation view of an alternative roller bearing support system.

DESCRIPTION OF THE PREFERRED EMBODIMENT

Figure 1:
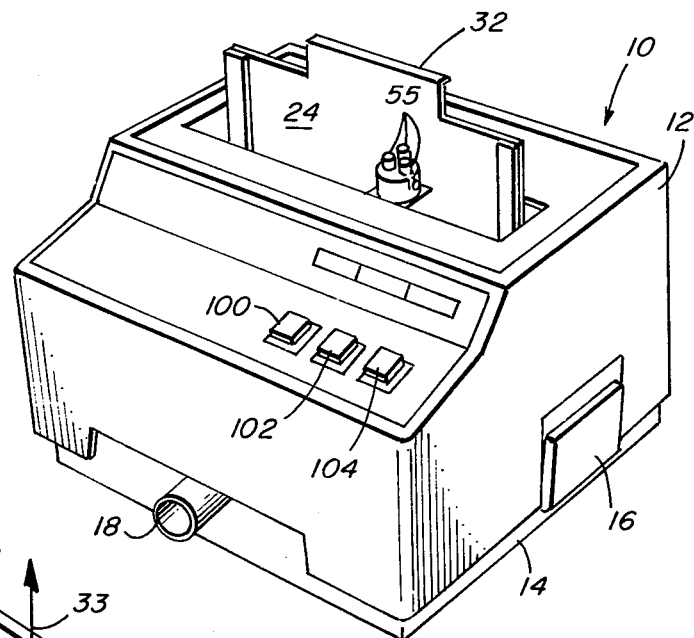
FIG. 1 is a perspective view of the spirometer disclosed herein.

Corresponding elements in the several figures of the drawing will be designated by the same reference numbers.

The recording spirometer 10 shown in FIG. 1 includes an upper housing portion 12 and a lower housing portion 14. The two housing portions 12 and 14 are held together tightly by a latching mechanism 16 of conventional design. Air is admitted into the spirometer 10 through an opening 18 in the lower housing portion 14. The spirometer 10 will now be described in more detail with reference to FIGS. 1, 2 and 3.

Disposed within the housing portions 12 and 14 is a pusher plate 20. The pusher plate 20, preferably made of molded plastic, is generally a flat plate with upturned sides. The pusher plate 20 is supported by an elongate supporting member 22. The pusher plate 20 is attached to the elongate supporting member 22 by means of screws (not shown). Attached by screws to the front of the supporting member 22 is a recording medium support plate 24. The plate 24 has lips 26, 28 and 30 which are adapted for holding a recording medium such as a piece of paper or cardboard (not shown). The recording medium support plate 24 also has a top portion 32 so that the plate 24 may be lifted manually for the expiratory and inspiratory measurements to be described hereinafter. The supporting member 22 is constrained to linear motion along an axis 33 by means of roller bearings 34, 36, 38 and 40 which are mounted on the upper housing 12. These rollers have tapered edges which are adapted to fit into a groove 42a and a groove 42b on opposite sides of the supporting member 22. In this way the pusher plate 20 and the supporting member 22 are constrained to substantially linear motion along the axis 33.

Disposed within the spirometer 10 and clamped between the upper and lower housing portions 12 and 14 is an elastomeric rolling seal 44 which is preferably made of molded rubber. The seal 44 creates an airtight chamber 46 bounded by the lower inside surface of the housing portion 14 and the seal 44. As air enters the chamber 46 through the opening 18, the rolling seal 44 and the pusher plate 20 will move upwardly within the spirometer 10. As this happens, the recording medium support plate 24 also moves upwardly. Because the supporting member 22 is attached to the pusher plate 20 substantially at its geometric center which is also the center of pressure for a flat plate, there will be little tendency for the pusher plate 20 to cock or deviate from straight line motion, and the roller bearings 34, 36, 38 and 40 assure that the pusher plate 20 does not stick or jam as it moves upwardly even in the presence of small force imbalances.

A marking assembly 48 is disposed in front of the recording medium support plate 24. The marking assembly 48 includes a base member 50 supporting a turret 52. The turret 52 is rotatable about an axis parallel to the axis 33 and includes three openings 54 which are adapted for holding marking instruments such as pens 55 having writing tips extending along axes perpendicular to the axis 33. The base member 50 is slidingly supported on a shaft 56 securely affixed to the upper housing portion 12. The base member 50 is also attached to a flexible, notched belt 58 carried on pulleys 60 and 62. The pulley 62 is driven by an electrical motor 64 of conventional design. In operation, the motor 64 is adapted for driving the marking assembly 48 laterally across the recording medium support plate 24 at a constant rate. Thus, the concurrent motion of the recording medium support plate 24 moving upwardly and the marking assembly 48 moving laterally creates a graph of volume as a function of time. In the present embodiment, the motion of the marking assembly 48 is begun by means of a microswitch 66. The microswitch 66 is maintained in an open circuit state as long as the pusher plate 20 is in its lowest position. The microswitch 66 is maintained in this open state by means of a bracket 68 attached to the backside of the recording medium support plate 24. As soon as the pusher plate 20 begins to move upwardly, the bracket 68 moves away from the microswitch 66 thereby closing the circuit and starting the lateral motion of the marking apparatus 48.

With reference to FIG. 3, it can be seen that the supporting member 22 has a slot 70 in its rear surface. A solenoid 72 is mounted on the upper portion of the housing 12. The solenoid 72 includes an armature 73 which is selectively movable along an axis perpendicular to the axis 33. When the solenoid 72 is activated, the armature 73 is in its extended position and the tip of the armature 73 engages the slot 70. When so engaged, the pusher plate 20 is supported at an intermediate position to perform the maximum voluntary ventilation test to be discussed below. The solenoid 72 is spring-loaded so that when it is not energized the armature 73 is in its retracted state and withdrawn from the slot 70.

When the pusher plate is supported at the intermediate position, apparatus is provided to keep the rolling seal 44 in contact with the pusher plate 20. If this were not provided for, the rolling seal 44 would sag away from the pusher plate 20 resulting in an inaccurate record of volume versus time. FIG. 4 illustrates the apparatus for maintaining the rolling seal 44 in contact with the pusher plate 20 during use while allowing the seal 44 and the plate 20 to be separated when desired such as for cleaning. The apparatus includes a ferromagnetic plate 80 which is attached to the rolling seal 44 by means of rivets 82. The plate 80 which is generally rectangular has portions cut away to reduce its weight. Disposed on the bottom side of the pusher plate 20 is an array of spaced apart permanent magnets 84. The location of the magnets 84 is selected to engage the ferromagnetic plate 80 when the pusher plate 20 is in contact with the rolling seal 44. In this way the seal 44 is prevented from sagging away from the pusher plate 20 during the spirometer 10 operation.

FIG. 5 illustrates an alternate suspension system for the supporting member 22. In this embodiment, the member 22 is supported by three rollers 90. Two of the rollers 90 are disposed on one side of the member 22 and the third roller 90 is disposed on the opposite side approximately half way between the other two rollers. It is recognized that other means are available to constrain the supporting member and the embodiments discussed herein should not be construed in a limiting sense.

The operation of the spirometer 10 will now be discussed with reference to FIGS. 1, 2, 3 and 4. The single breath, forced vital capacity test will be described first. For this test the pusher plate 20 begins in its lowest position. A piece of paper, cardboard, or other recording medium (not shown) is placed on the recording medium support plate 24 and held in position by lips 26, 28 and 30. One or more pens 55 are placed in the openings 54 in the turret 52, and the marking assembly 48 is placed in its initial position to the right in FIG. 2. The turret 52 is then rotated to position one of the pens 55 for marking engagement with the recording medium. A power switch 100 is then placed in the "on" position, after which a human subject is instructed to exhale into a tube (not shown) which connects with the opening 18. In the automatic mode of operation, as soon as the pusher plate 20 begins to move, the microswitch 66 will close a circuit starting the motor 64 which in turn drives the marking assembly 48 across the recording medium plate 24 at a constant rate. As the subject exhales, the pusher plate 20 rises carrying with it the recording medium support plate 24 so as thereby to create a graph or plot of the volume of expired air as a function of time. If it is important or desirable to record the very beginning of exhalation, that is, the period before the microswitch 66 is activated, the motor 64 may be activated manually by means of a switch 102 shortly before the subject is instructed to exhale.

In addition to the single breath test just described, another important test is the maximum voluntary ventilation measurement. In this test, the subject is instructed first to exhale and then to inhale deeply and rapidly. Because both inhalation and exhalation are parts of this test, the pusher plate 20 must be able to move both up and down. Because the volume exhaled in the first part of the test may be less than the volume inhaled in the second part, the pusher plate 20 cannot simply start in its lowest position as in the single breath test since the completion of inhalation would be prevented in this circumstance. Thus, in order to accomplish this test, the pusher plate 20 must begin the test at an intermediate position. In the embodiments illustrated in the figures, the intermediate position is such that the volume in the airtight chamber is approximately 1.5 liters at the beginning of the test. The maximum volume is around eight liters. To begin the maximum voluntary ventilation test a switch 104 is depressed and held down. Depressing the switch 104 activates the solenoid 72 so that the armature 73 is in its extended state. The recording medium support plate 24 is then grasped manually by the upwardly extending portion 32 and lifted until the armature 73 engages the slot 70. The recording medium support plate 24 is then released so that the upper part of the slot 70 rests on the extended armature 73 of the solenoid 72. At this time, the switch 104 is released so that the solenoid 72 is deactivated. Although the solenoid 72 is springloaded so that it tends to return to its unextended state when deactivated, it is prevented from doing so by the friction between the slot 70 and the armature 73 of the solenoid 72 due to the weight of the pusher plate 20 and supporting member 22. Thus, the pusher plate 20 remains at the intermediate position after the switch 104 is released, and the seal 44 is prevented from sagging as discussed above. The motor 64 is then activated by depressing the switch 102 and the subject is instructed first to exhale and then to inhale. As soon as the subject begins to exhale, the pusher plate 20 rises so that the friction force holding the solenoid 72 in its extended state vanishes, and the solenoid resumes its retracted state. The pusher plate continues to rise as the subject exhales and then begins to fall as the subject inhales. Because the solenoid 72 is in its unextended state, the pusher plate is again free to travel to its lowest position. By this procedure, a graph of both exhalation and inhalation is created.

Figure 2:
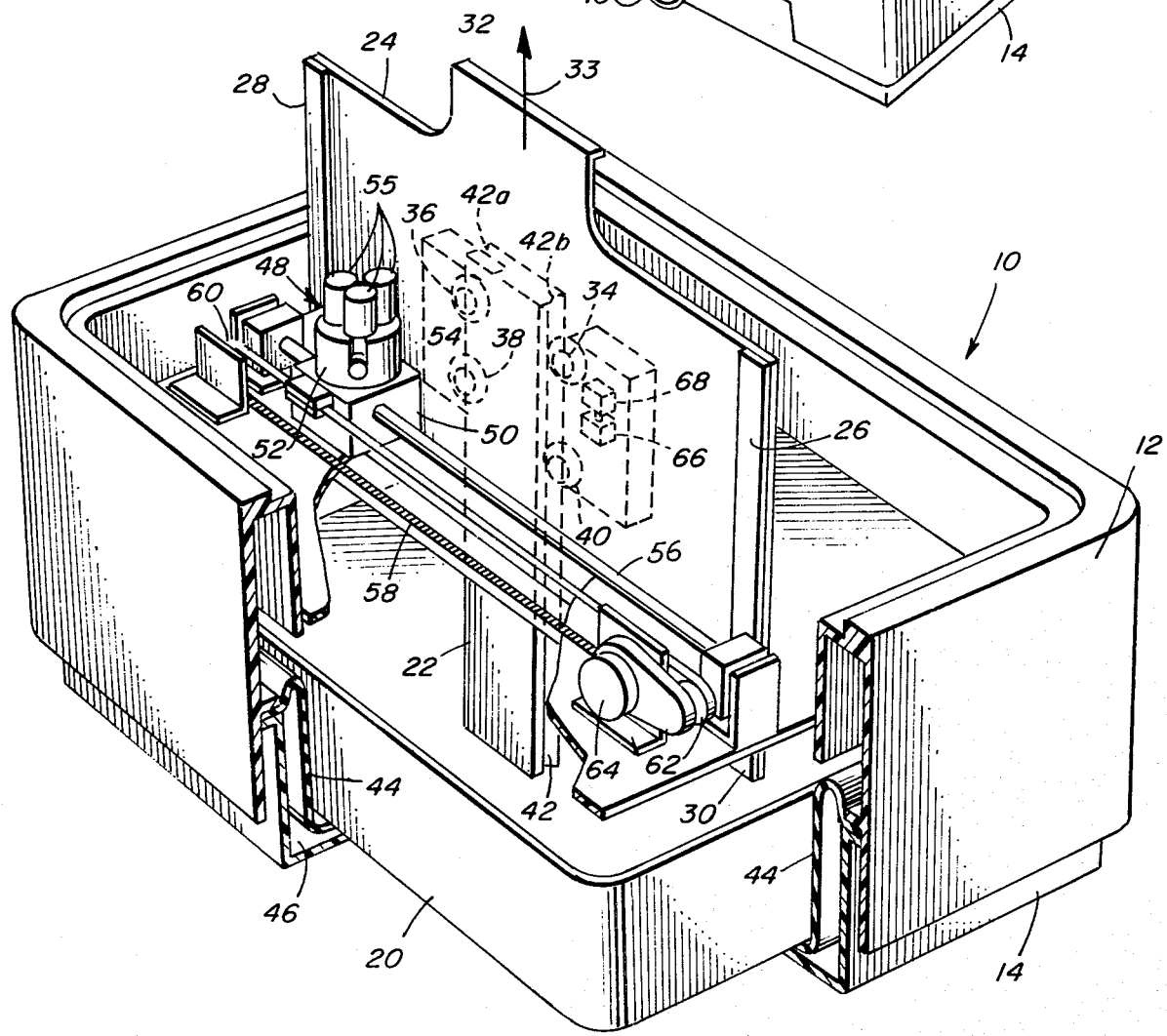
FIG. 2 is a perspective view, partially cut away, of the spirometer of FIG. 1.

It will often be desirable to conduct several tests with a single subject, for example, a single breath test followed by the maximum voluntary ventilation test. In this case it is convenient to mark the recording medium in different colors for each test for ease in evaluating the results. The turret 52 allows such a change of color without the necessity for recalibrating the position of the marking instrument with respect to the recording medium. As shown in FIG. 2, three pens 55 may be mounted on the turret 52. After the single breath test is performed, for example, the turret 52 is simply rotated so that another marking instrument having a different color is in position for marking the recording medium. Because the turret 52 is rotatable, each of the pens is calibrated to engage the recording medium at the proper location. The pens will remain properly located when rotated into position.

It is thus seen that the objects of this invention have been achieved in that there has been disclosed a recording spirometer which is reliable, accurate and simple to construct. Furthermore the spirometer disclosed herein is capable of performing not only a single breath expiratory test but also tests requiring both exhalation and inhalation. Although this invention has been described with reference to its preferred embodiments, it is understood that modifications and variations will occur to those skilled in the art, and it is intended that all such variations and modifications are encompassed within the scope of the appended claims.

What is claimed is:

1. A recording spirometer comprising:
   a housing including an upper portion and a lower portion;
   a pusher plate having a top side and a bottom side disposed within said housing;
   sealing means for creating an airtight seal between said pusher plate and said housing;
   a single elongate supporting member affixed to and extending from the top side of said pusher plate;
   bearing means supported by said upper portion of said housing and including means for engaging said single supporting member to constrain said supporting member and the affixed pusher plate to substantially linear motion along a reference axis and to substantially eliminate the potential jamming of the pusher plate and to create beneath said bottom side of said pusher plate an airtight chamber whose volume varies with the position of said pusher plate along said axis;

an opening in said lower portion of said housing adapted for the introduction of exhaled air into said airtight chamber;

a recording medium support element which supports a recording medium mounted on said supporting member; and apparatus for marking a record on said recording medium, said marking apparatus including means for driving said marking apparatus at a constant rate along a axis perpendicular to said reference axis whereby concurrent movement of said pusher plate and said marking apparatus creates a graph of the volume of said chamber as a function of time.

2. The apparatus of claim 1 wherein said sealing means comprises a molded elastomeric rolling seal disposed adjacent to said bottom side of said pusher plate, said seal having edges clamped between said upper and lower housing portions.

3. The apparatus of claim 1 wherein said bearing means comprises a first pair of spaced apart rollers disposed on one side of said elongate supporting member and a second pair of spaced apart rollers disposed on an opposite side of said elongate supporting member, said rollers fitting into grooves in said sides of said elongate supporting member.

4. The apparatus of claim 1 wherein said bearing means comprises a pair of spaced apart rollers disposed on one side of said elongate supporting member and a single roller disposed on an opposite side of said elongate supporting member approximately half way between said pair of spaced apart rollers, said rollers fitting into grooves in said sides of said elongate supporting member.

5. A recording spirometer comprising:

a housing;

a pusher plate having a top side and a bottom side disposed within said housing;

sealing means for creating an airtight seal between said pusher plate and said housing;

bearing means for constraining said pusher plate to substantially linear motion along a reference axis to create beneath said bottom side of said pusher plate an airtight chamber whose volume varies with the position of said pusher plate along said axis;

an opening in said housing adapted for the introduction of exhaled air into said airtight chamber;

a recording medium suport elements which supports a recording medium interconnected with said pusher plate to move along said reference axis;

marking apparatus comprising a rotatable turret adapted for holding a plurality of marking instruments for sequentially marking a record on said recording medium; and means for driving said marking apparatus at a constant rate along an axis perpendicular to said reference axis, whereby concurrent movement of said pusher plate and said marking apparatus creates a graph of the volume of said chamber as a function of time.

6. The apparatus of claim 1 or claim 5 wherein said marking apparatus is slidingly supported on a shaft affixed to said housing and is moved across said recording medium support element by motor driven flexible belt means.

7. The apparatus of claim 6 further including switch means for activating said motor driven belt means, said switch means mounted for activation upon movement of said pusher plate.

8. A recording spirometer for measuring maximum voluntary ventilation comprising:

a housing including an upper portion and a lower portion;

a pusher plate having a top side and a bottom side disposed within said housing;

sealing means for creating an airtight seal between said pusher plate and said housing;

an elongate supporting member having a front side and a back side affixed to and extending from the top side of said pusher plate, said supporting member having a slot in its said back side;

bearing means supported by said upper portion of said housing and including means for engaging said supporting member to constrain said supporting member and the affixed pusher plate to substantially linear motion along a reference axis over a dynamic range to create beneath said bottom side of said pusher plate an airtight chamber whose volume varies with the position of said pusher plate along said axis;

an opening in said lower portion of said housing adapted for the passage of exhaled and inhaled air into and out of said airtight chamber;

a recording medium support element which supports a recording medium mounted on said front side of said supporting member to move linearly with said pusher plate;

apparatus for marking a record on said recording medium, said marking apparatus including means for driving said marking apparatus at a constant rate along an axis perpendicular to said reference axis;

means for supporting said pusher plate at an intermediate position within its said dynamic range at the beginning of the measurement of said maximum voluntary ventilation; and means for maintaining said sealing means in intimate contact with said pusher plate throughout said measurement, whereby concurrent movement of said pusher plate and said marking apparatus creates a graph of the volume of said chamber as a function of time.

9. The apparatus of claim 8 wherein said marking apparatus is slidingly supported on a shaft affixed to said housing and is moved across said recording medium by motor driven belt means.

10. The apparatus of claim 8 wherein said marking apparatus comprises a rotatable turret adapted for holding a plurality of marking instruments for sequentially marking said recording medium.

11. The apparatus of claim 8 wherein said bearing means comprises a first pair of spaced apart rollers disposed on one side of said elongate supporting member and a second pair of spaced apart rollers disposed on an opposite side of said elongate supporting member, said rollers fitting into grooves in said sides of said elongate supporting member.

12. The apparatus of claim 8 wherein said bearing means comprises a pair of spaced apart rollers disposed on one side of said elongate supporting member and a single roller disposed on an opposite side of said elongate supporting member approximately half way between said pair of spaced apart rollers, said rollers fitting into grooves in said sides of said elongate supporting member.

13. A recording spirometer for measuring maximum voluntary ventilation comprising:

a housing including an upper portion and a lower portion;

a pusher plate having a top side and a bottom side disposed within said housing;

sealing means for creating an airtight seal between said pusher plate and said housing;

an elongate supporting member having a front side and a back side affixed to and extending from the top side of said pusher plate, said supporting member having a slot in its said back side;

bearing means supported by said upper portion of said housing and including means for engaging said supporting member to constrain said supporting member and the affixed pusher plate to substantially linear motion along a reference axis over a dynamic range to create beneath said bottom side of said pusher plate an airtight chamber whose volume varies with the position of said pusher plate along said axis;

an opening in said lower portion of said housing adapted for the passage of exhaled and inhaled air into and out of said airtight chamber;

a recording medium support element which supports a recording medium mounted on said front side of said supporting member to move linearly with said pusher plate;

apparatus for marking a record on said recording medium, said marking apparatus including means for driving said marking apparatus at a constant rate along an axis perpendicular to said reference axis;

means for supporting said pusher plate at an intermediate position within its said dynamic range at the beginning of the measurement of said maximum voluntary ventilation wherein said means for supporting said pusher plate at an intermediate position within its dynamic range comprises a solenoid disposed on said housing so as to engage in its extended state said slot in said supporting member; and means for maintaining said sealing means in intimate contact with said pusher plate throughout said measurement, whereby concurrent movement of said pusher plate and said marking apparatus creates a graph of the volume of said chamber as a function of time.

14. A recording spirometer for measuring maximum voluntary ventilation comprising:

a housing including an upper portion and a lower portion;

a pusher plate having a top side and a bottom side disposed within said housing;

sealing means for creating an airtight seal between said pusher plate and said housing;

an elongate supporting member having a front side and a back side affixed to and extending from the top side of said pusher plate, said supporting member having a slot in its said back side;

bearing means supported by said upper portion of said housing and including means for engaging said supporting member to constrain said supporting member and the affixed pusher plate to substantially linear motion along a reference axis over a dynamic range to create beneath said bottom side of said pusher plate an airtight chamber whose volume varies with the position of said pusher plate along said axis;

an opening in said lower portion of said housing adapted for the passage of exhaled and inhaled air into and out of said airtight chamber;

a recording medium support element which supports a recording medium mounted on said front side of said supporting member to move linearly with said pusher plate;

apparatus for marking a record on said recording medium, said marking apparatus including means for driving said marking apparatus at a constant rate along an axis perpendicular to said reference axis;

means for supporting said pusher plate at an intermediate position within its said dynamic range at the beginning of the measurement of said maximum voluntary ventilation; and means for maintaining said sealing means in intimate contact with said pusher plate throughout said measurement wherein said sealing means comprises a molded elastomeric rolling seal having an inside surface adjacent said pusher plate and said means for maintaining said sealing means in intimate contact with said pusher plate comprises:

(1) a ferromagnetic plate member secured to the inside surface of said elastomeric seal; and (2) a plurality of spaced-apart permanent magnets secured to said bottom side of said pusher plate and located to engage said plate member, whereby concurrent movement of said pusher plate and said marking apparatus creates a graph of the volume of said chamber as a function of time.

* * * * *